United States Patent [19]

Birtwell

[11] 4,222,384
[45] Sep. 16, 1980

[54] CATHETER

[75] Inventor: William Birtwell, North Scituate, R.I.

[73] Assignee: Biomedical Engineering Associates, Inc., Boston, Mass.

[21] Appl. No.: 849,961

[22] Filed: Nov. 9, 1977

Related U.S. Application Data

[63] Continuation of Ser. No. 659,832, Feb. 20, 1976, abandoned.

[51] Int. Cl.³ .............................................. A61M 25/00
[52] U.S. Cl. ................................................... 128/349 B
[58] Field of Search ............ 128/349, 349 B, 349 BV, 128/350, 344, 246

[56] References Cited

U.S. PATENT DOCUMENTS

| | | | |
|---|---|---|---|
| 2,912,981 | 11/1959 | Keough | 128/349 B |
| 3,547,126 | 12/1970 | Birtwell | 128/246 X |
| 3,734,100 | 5/1973 | Walker et al. | 128/349 B X |
| 3,832,253 | 8/1974 | Palma et al. | 128/349 BV |
| 3,833,003 | 9/1974 | Taricco | 128/349 B |
| 3,850,720 | 11/1974 | Collins | 128/349 B |
| 3,926,705 | 12/1975 | Todd | 128/349 B X |

*Primary Examiner*—Stephen C. Pellegrino
*Attorney, Agent, or Firm*—Wolf, Greenfield & Sacks

[57] ABSTRACT

An improved Foley-type urethal catheter is formed from silicone rubber. The tip of the catheter is molded in one integral piece to include drainage eyes and a rearwardly extending balloon portion. The rubber of the balloon portion is substantially more elastic than the tip. The trailing portion of the catheter includes an elongated tubular body attached to and extending rearwardly from the tip and to which the rear end of the balloon portion of the tip is attached. A drainage lumen extends from the tip through the body to the trailing end of the catheter and a plurality of inflation lumens also extend through the catheter body from the inflatable balloon portion to the trailing end of the body. The elongate catheter body is formed from an inner tube and an outer, surrounding sleeve to enable the stiffness of the catheter to be controlled carefully during manufacture. The sleeve and inner core of the catheter and rear end of the balloon are joined in a shoulderless, smooth construction.

8 Claims, 13 Drawing Figures

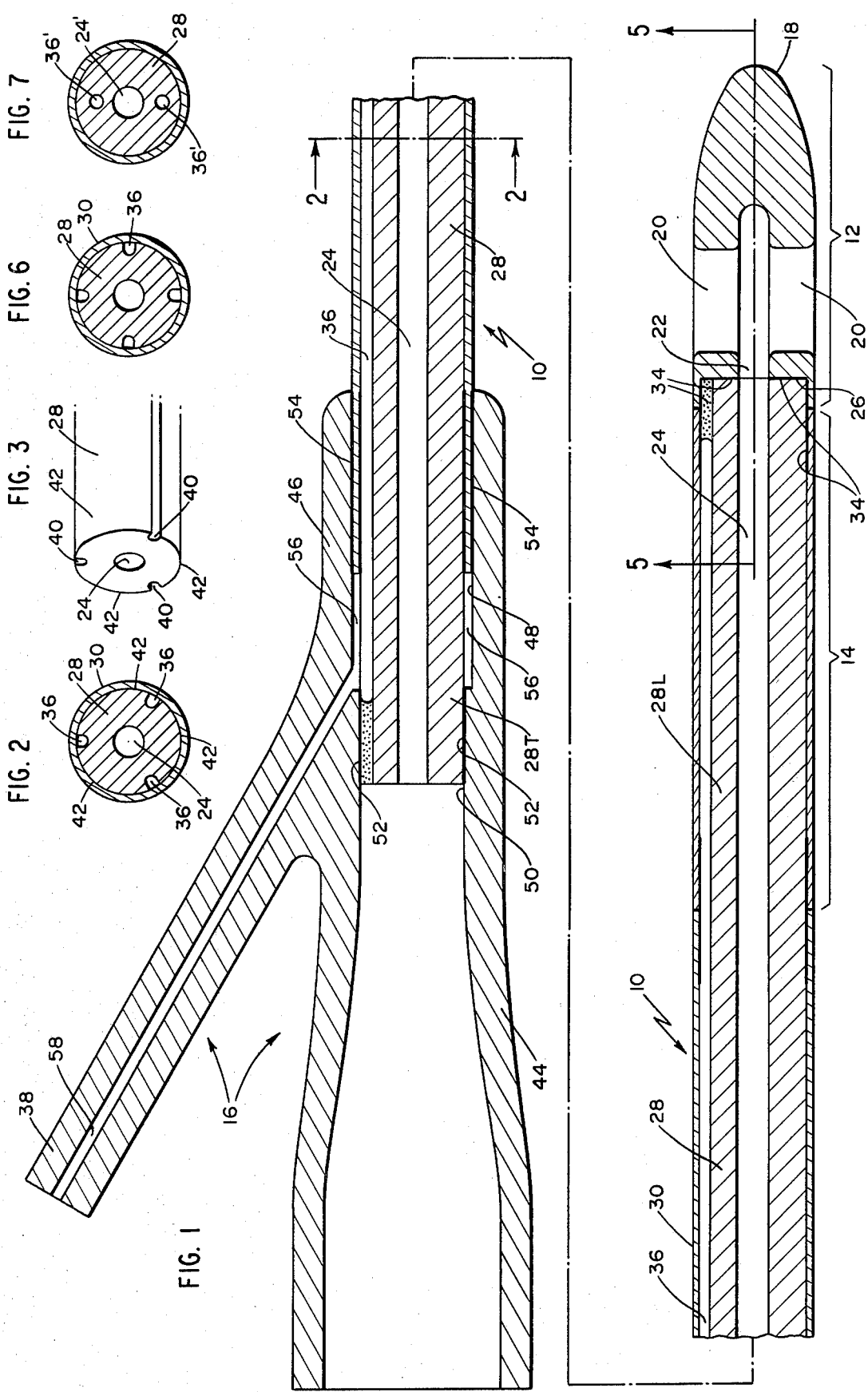

CATHETER

This is a continuation of application Ser. No. 659,832, filed Feb. 20, 1976 now abandoned.

BACKGROUND OF THE INVENTION

This invention relates to catheters and particularly to urethral drainage catheters of the balloon type. Such catheters are used extensively for bladder drainage, for example, in cases of patient incontinence or when, for any reason, he cannot release urine from his bladder because of a constriction in his urethra. The catheter is introduced into the bladder via the urethra which, in the male, is a relatively tortuous tube of varying cross-sectional dimensions which is normally collapsed along most of its length. The upper portion of the urethra has sphincters or valves where it enters the bladder neck. In the female, the urethra is shorter and straighter but otherwise functionally the same.

At best, the use of such a catheter is quite uncomfortable to the patient. In order to minimize the discomfort and to facilitate insertion and proper placement of the catheter, it should be of smooth and rounded contour and should be as slender as possible. The drainage eyes in the tip should be shaped to provide flow passage for the urine and should have no sharp edges. There should be no shoulders on the catheter facing either in the forward or in the backward direction which might hinder insertion or removal of the catheter. While the catheter should bend easily to follow the tortuous path of the urethra, it also should have good cross-sectional stability to prevent kinking and collapse in the areas of the urethra which may be constricted.

When properly positioned, the tip of the catheter protrudes into the patient's bladder. Under normal circumstances, the bladder is emptied voluntarily from time to time by controlling the sphincter muscles. However, when the catheter is in place, the bladder is drained continually and thus is as empty as the location of the drainage holes or eyes of the catheter tip permits. When empty, the bladder walls rest on the catheter tip and a smooth tip will minimize the likelihood of irritation and trauma to the bladder wall. It also is desirable that the drainage eyes in the tip be located as low in the bladder as possible to minimize the amount of undrainable urine in the bladder.

In order to securely anchor the catheter in place, the catheter includes an expandable balloon located behind the drainage eyes. The balloon is inflated only after the catheter is in proper position. The balloon is inflated (to anchor) or deflated (for removal) by means of elongate inflation lumens formed through the body of the catheter and which communicate with the balloon.

The manufacture of urethral catheters having the foregoing desirable characteristics has not been without difficulty. In general, such catheters have been formed from latex and in a complicated, time-consuming, dipping process well known to those skilled in the art. Because of the relatively flexible and elastic nature of the latex, such catheters tend to bend or kink. As a result it has not been possible to form the various openings and passageways in the catheter to be as large as would be desirable because that would further reduce the stiffness of the catheter. These limitations also restrict the number of inflation lumens which can be employed. Typically, there are no more than two inflation lumens and sometimes there is only one. This can result in serious difficulties when it is desired to remove the catheter should the inflation lumens become blocked and fail to permit deflation of the balloon. Still another difficulty with prior urethral catheters is that the latex material can react with the urine and is quite wettable which makes for patient discomfort when the catheter is advanced within the urethra. Also among the difficulties with latex catheters is that the balloons sometimes malfunction, by rupturing or failing to deflate.

These and other commonly encountered difficulties of latex urethral catheters can be minimized significantly by making the catheter from a more biologically inert material, such as silicone rubber and I have made and described such an invention in my U.S. Pat. No. Re. 27,910. As described more fully in that patent, a catheter tip and balloon flap are molded as an integral, one-piece unit which is attached to the leading end of the catheter tube, also made from silicone rubber. The resulting catheter is shoulderless, is of good cross-sectional stability and enables the various openings and lumens to be of an enlarged size. Additionally, the catheter described in my foregoing patent is more easily and economically manufactured than the typical prior dipped latex-type catheters.

While the catheter described in my foregoing U.S. patent is a significant advance over the prior latex catheters, it nevertheless has required some compromise because the tip preferably is relatively inelastic and stiff while the balloon portion desirably is elastic and resilient. Where the tip and balloon are molded from the same material in a one-piece, unitary construction, the elasticity and stiffness of the tip and balloon material are the same. It is among the primary objects of the present invention to provide a urethral catheter having a one-piece, molded tip and integral balloon in which each has the ideal properties of stiffness and/or elasticity.

SUMMARY OF THE INVENTION

The tip and balloon portion are molded in a single integral piece in a suitable mold but in a manner in which the tip portion of the mold is loaded with a parison of silicone rubber which will be stiff when cured and with the balloon portion of the mold being loaded with a parison of compatible silicone rubber which will be more elastic when cured. During the molding procedure, the balloon and tip materials merge and fuse to form a shoulderless, one-piece, integral unit.

The invention also relates to an improved construction for the trailing, elongated body of the catheter by which the cross-sectional stability of the elongate portion may be very accurately controlled. The body is formed in a two-piece construction which includes an inner core through which the drainage lumen extends and an outer sleeve which surrounds the inner core. One or more inflation lumens may be formed through the inner core or, in an alternative embodiment, by elongate grooves formed on the outer surface of the core which cooperate with the surrounding inner surface of the sleeve. The latter configuration permits the use of a plurality of inflation lumens, for example, three or four, which virtually eliminates the possibility of total inflation lumen failure. The cross-sectional stability is controlled very accurately by extruding the inner core and sleeve from silicone rubber materials having different selected properties of stiffness and elasticity. The properties of the combined inner core and outer sleeve will depend on the selection of materials.

The one-piece molded tip and balloon and trailing catheter body then are attached to each other with the trailing end of the balloon merging smoothly into the catheter body to define a completely shoulderless construction.

It is among the general objects of the invention to provide an improved silicone rubber molded urethral catheter.

Another object of the invention is to provide a balloon catheter in which the tip is of one-piece, molded integral construction with the balloon and in which the elasticity of the balloon portion is substantially greater than that of the tip portion.

Another object of this invention is to provide a drainage catheter having a tip which is not subject to collapse.

Another object of this invention is to provide a urethral drainage catheter which has no shoulders or other protrusions which might interfere with its movement through the urethra.

A further object of this invention is to provide a catheter made of materials which are physiologically acceptable and which do not deteriorate from contact with urine.

Another object of this invention is to provide a catheter having a plurality of inflation lumens in the wall of the elongated body or tube to provide greater assurance of balloon deflation.

A further object of the present invention is to provide a urethral drainage catheter having a balloon made of a soft easily stretchable but non-tearable material which may be inflated by relatively low pressures.

Still another object of the invention is to provide a two-piece construction for a catheter body including a core and a surrounding sleeve which are made from silicone rubbers of different stiffness to enable precise control of the cross-sectional stability of the body.

DESCRIPTION OF THE DRAWINGS

These and other objects and features of this invention along with its incident advantages will be better understood and appreciated from the following further description thereof, selected for purposes of illustration and shown in the accompanying drawings, wherein:

FIG. 1 is a sectional illustration of a drainage catheter constructed in accordance with this invention;

FIG. 2 is a cross-sectional view of the drainage catheter in FIG. 1 as seen along the line 2—2, showing the inflation lumens defined by grooves formed in the tubular core of the elongated body;

FIG. 3 is a perspective view of the inner tubular core of the catheter body illustrating further the lumen-defining grooves;

FIG. 6 is an illustration similar to FIG. 2 showing a catheter tube with four inflation lumens;

FIG. 7 is a cross-sectional view of another embodiment of the elongated body in which the inflation lumens are formed within the core;

DESCRIPTION OF THE PREFERRED EMBODIMENT

Figure 4:
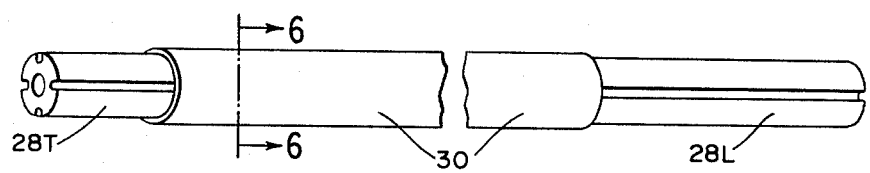
FIG. 4 is an illustration of the ends of a catheter tube having four inflation lumens and made in accordance with the invention, before attachment to the tip and funnel.

As shown in FIGS. 1-4, the drainage catheter includes an elongated tubular body 10, a tip assembly which includes a tip 12 with integral balloon portion 14, and a funnel 16 attached to the trailing end of the body 10. As mentioned above, it is preferred to fabricate all of the elements of the catheter from silicone rubber because of its inert, non-wetting, stiffness and other desirable characteristics as described.

The tip 12 and balloon portion 14 are formed in a mold having a mold cavity of corresponding shape. As will be described below in more detail, the mold cavity is loaded with parisons of putty-like, uncured silicone rubber. The tip portion of the mold cavity is loaded with a silicone rubber material which, when cured, will be relatively stiff and inelastic while the more rearward portion of the mold cavity which defines the balloon is loaded with a silicone rubber material which, when cured, will be of significantly greater elasticity. For example, the balloon region of the mold cavity may be loaded with a silicone rubber compound commercially available from General Electric Company and identified as its No. 7000 or the material identified as No. S-2000 from the Dow Chemical Company. The silicone rubber materials for the balloon 14 and tip 12 are completely compatible with each other, and display the same desirable properties except that the balloon portion 14 will be substantially more elastic than the tip portion 12. For example, the balloon material described may be stretched up to nine or ten times its original dimensions while maintaining adequate tear strength. Additionally, substantially less inflation pressure is required in order to inflate the balloon portion 14 which is a very desirable feature. By requiring less pressure to inflate and expand the balloon, the catheter is easier and safer to use. In contrast, the tip portion 12 of the tip assembly may be made from a silicone rubber compound which may be approximately half as elastic, and may be capable of being stretched approximately three to five times its original dimensions.

The tip 12 has a smooth, rounded leading end 18 to facilitate insertion and movement through the tortuous and normally collapsed urethra. A pair of drainage eyes 20 extend transversely through the tip 12 and communicate through an opening 22 in the rearwardly facing end of the tip 12 with the centrally located drainage lumen 24 which extends through the catheter body 10. The rearwardly facing end of the tip 12 is formed to define a shoulder 26 which surrounds the opening 22 and which receives the leading end of the main body of the catheter 10 as will be described. The balloon portion 14 extends rearwardly from the rear end of the tip 12 and is fused into a single, integral unit with the tip portion 12 during the molding process. The outer diameter of the molded balloon portion 14 is the same as the rear end of the tip portion 12 so that after the molding process the balloon portion 14 is, in effect, a smooth, continuous, shoulderless and integral rearward extension of the tip portion 12, although having substantially more elastic properties.

The trailing, elongate body portion 10 of the catheter is of two-piece construction and includes an inner core 28 and an outer sleeve 30 which surrounds the inner core 28. The inner core 28 is longer than the outer sleeve 30 and protrudes forwardly beyond the leading end of the outer sleeve 30, as suggested at 28L in FIG. 4. Similarly, the other end of the inner core 28 protrudes rearwardly beyond the trailing end of the outer sleeve 30 in like manner as suggested at 28T in FIG. 4. The forward end 28L of the inner core 28 extends into the balloon portion 14 and is butted against the shoulder 26 of the tip 12 and the outer sleeve 30 butts against the rearward, trailing edge of the balloon portion 14. The forwardmost end 28L of the core 28 is adhesively bonded to the shoulder 26 of the tip 12 and to the forwardmost region of the balloon portion 14 as suggested at 34 and in a manner which will be described in more detail below.

Figure 5:
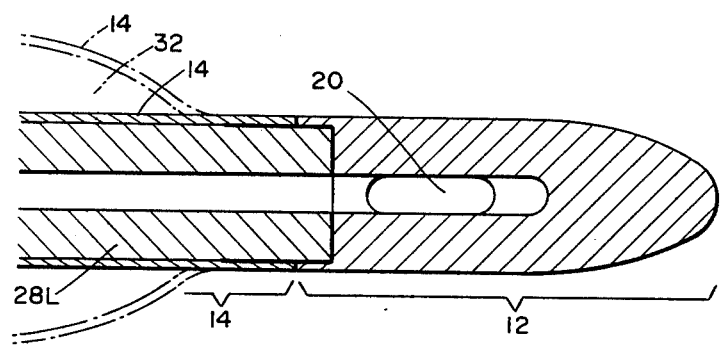
FIG. 5 is a sectional illustration of the tip end of the catheter as seen along the line 5—5 of FIG. 1.

The wall thickness of the outer sleeve 30 is the same as the thickness of the balloon portion 14 so that when the balloon portion 14 and sleeve 30 butt against each other they will define a smooth and uninterupted cylindrical external surface, free of any shoulders or other surface irregularities. After the tip 12 and inner core 28 have been cementaciously attached, the rear end of the balloon portion 14 also is cemented at the shoulder region between the forwardly protruding end 28L of the inner core 28 and surrounding balloon portion 14 defines an inflatable annular space 32 as suggested in phantom in FIG. 5.

The balloon portion 14 is inflated and deflated at means of inflation lumens 36 which extend through the catheter tube 10 and communicate the annular inflatable balloon region 32 with the inflation branch 38 of the funnel. FIGS. 1-3 shows a preferred lumen construction which is usable particularly in connection with the core and sleeve structure of the catheter body 10 described above. In this embodiment, the inner core 28 is extruded in a manner to define a plurality of external grooves 40 extending along the length of the inner core 28. The grooves 40 may be considered as being separated by lands 42 defined at the outer surface of the inner core 28. When the sleeve 30 is subsequently slipped over the inner core 28, it will cooperate with the grooves 40 and lands 42 to define the plurality of inflation lumens 36. The outer sleeve 30 is cemented to the intermediate land portions 42 only at its forward and rearward ends and in a manner which will not obstruct flow of the inflating medium through the lumens 36. It may be noted that the inflating medium typically is a sterile liquid such as distilled water or a saline solution. The use of the substantial number (more than two) of inflation lumens 36 reduces the chance of complete lumen blockage during deflation to practically nil. While the illustration in FIGS. 1-3 shows three inflation lumens, it may be desirable to employ four or more of such lumens as shown in FIGS. 4 and 6, the three lumens in the drawing have been selected for clarity of illustration.

FIG. 7 shows an alternative inflation lumen configuration in which the inflation lumens 36' are formed entirely within the wall of the inner core 28. This type of inflation lumen configuration is somewhat like that shown in my U.S. Pat No. Re. 27,910 and requires that additional holes be formed in the wall of the inner core 28 to communicate the inflation lumens 36' with the inflatable annular space 32 within the balloon portion 14. These inflation lumens 36' may be formed in the inner core wall 28 during its extrusion. This type of lumen construction may, in some instances, present some problems because it necessarily weakens the catheter wall and it has not been uncommon in prior urethral catheters to increase the wall thickness at least about the region of the inflation lumens to prevent the wall from rupturing under inflation pressure. Increasing the wall thickness about the lumens 36', however, may require a reduction in the size of the drainage lumen 24' which is undesirable.

Significant advantages result from the inner core-outer sleeve construction of the catheter body, whether the inflation lumens are formed by grooves 40 in the outer surface of the outer core 28 or are wholly contained within the inner core 28 as shown in FIG. 7. The two-piece construction of the catheter body 10 also enables the stiffness and cross-sectional stability of the catheter tube 10 to be controlled far more effectively than with earlier catheters. For example, the inner core 28 may be extruded from a silicone rubber compound having relatively high degree of stiffness as compared to the material of the outer sleeve 30 so that the combination of materials may provide the ideal resultant stiffness for the composite catheter. This is to be constrasted with prior urethral catheters in which the stiffness of the catheter tube was controlled by varying the wall thickness of the tube. However, with prior devices the permitted range of wall thicknesses was limited because of the maximum limits imposed on the outer diameter of the tube (a function of urethra size) and the desirability of having a drainage lumen as large as possible. With the present invention, catheters of various stiffnesses can be made without compromising the cross-sectional dimensions of the catheter by selecting a suitable combination of materials for the inner core and outer sleeve. By way of example, the outer sleeve 30 may be formed from the same material as that from which the balloon portion 14 is formed or may be formed from a different material, displaying an elasticity intermediate that of the balloon portion 14 and the inner core 28. Preferably, the material from which the sleeve 30 is made is somewhat less elastic than the balloon portion 14 to insure that fluid pressure in the inflation lumens will not cause the sleeve 30 to expand during inflation under ordinary conditions. The core and sleeve catheter tube construction also enables more than two inflation lumens to be formed wholly within the core without adversely affecting the cross-sectional stability of the catheter tube. Also, with the core and sleeve construction, the inflation lumens may be located more closely to the drainage lumen which results in a thicker outer wall and increases the resistance of the catheter to compression from external constricting forces.

The trailing end of the catheter includes a funnel 16 which also is molded in a single piece from silicone rubber. The funnel 16 has an inflation branch 38 and a drainage branch 44 which merge in a neck 46. The forward, neck end of the funnel 16 has a bore 48 to receive the trailing end of the outer sleeve 30 of the catheter body 10. The rear end 28T of the catheter core 28 extends into a reduced diameter bore 50 which communicates with the drainage lumen 24. The rear end of the core 28 is cemented to the bore 50 as indicated at 52 and the rear end of the sleeve 30 is cemented to the bore 48 as indicated at 54. When assembled, the rear end of the sleeve 30 is spaced from the juncture of the bores 48, 50 of the funnel 16 to define an annular space 56 which serves as an inflation manifold about the inner core 28 in communication with the inflation passage 58 in the inflation branch 38.

Figure 8:
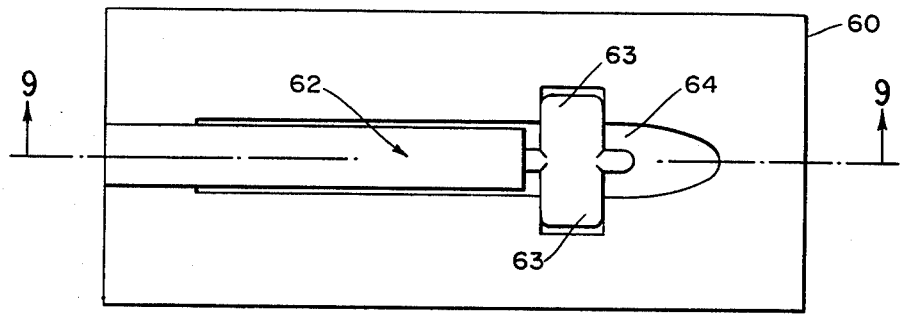
FIG. 8 is a plan view of the bottom half of the mold for making the catheter tip with the mold core in place.
Figure 9:
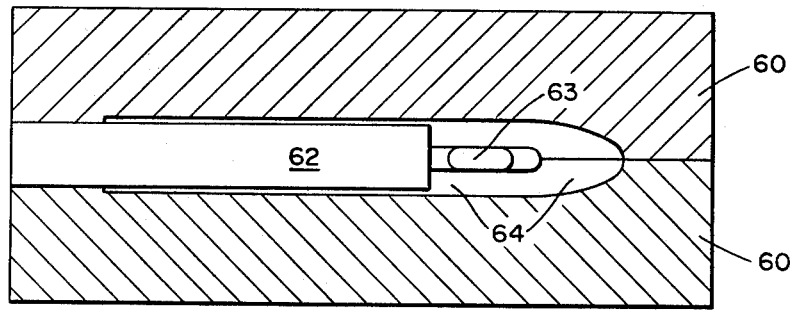
FIG. 9 is a sectional elevation through the assembled mold, including the upper half of the mold as seen along the line 9—9 of FIG. 8.
Figure 10:
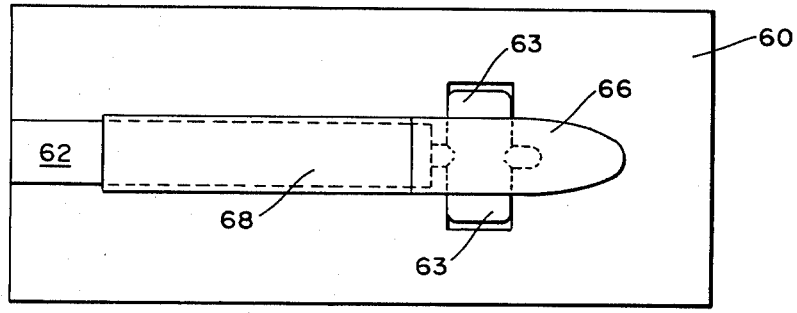
FIG. 10 is an illustration similar to FIG. 8 showing the parisons of putty-like molding material wrapped about the mold core and in place in the bottom half of the mold.

FIGS. 8-13 illustrate the method by which the catheter is molded and assembled. The mold for the integral tip and balloon portion includes two mold halves 60, a generally T-shaped mold core 62 which, when assembled and closed, define an enclosed mold cavity of the intended shape (FIGS. 8 and 9). FIG. 10 is an illustration of the loaded mold with one of the mold halves removed for clarity of illustration. In FIGS. 8-10, vent holes, screws (if employed), registration pins and other mold elements commonly employed in molding procedures have been omitted, also for purposes of clarity. A putty-like parison 66 (FIG. 10) of uncured stiff silicone rubber compound which will form the tip 12 is loaded into the tip region 64 of the mold cavity or may be wrapped about the tip end of the mold core 62. A parison 68 of putty-like silicone rubber compound which will result in a more elastic rubber is wrapped about the rearward portion of the more core 62. The mold sections are assembled and heated to cure the materials and to cause the balloon and tip parisons 66, 68 to fuse together to form the integral one-piece unit. It should be noted that the tip portion parison 66 and balloon portion parison 68 fuse and merge together in an integral, one-piece shoulderless unit and that after the molding procedure has been completed there is no remaining clear line of abuttment of the balloon and tip portions. For purposes of illustration and clarity, the drawings show an abuttment line (for example at 67 in FIG. 5) merely to illustrate the region where the balloon and tip portions of the tip assembly are merged.

After the tip has been molded and cured, the mold core 62 with the molded tip assembly thereon, is removed from the mold halves. The integral one-piece tip assembly is removed by stretching it to elastically enlarge one of the drainage eyes to enable the forwardmost tip of the core 62, including the drainage eye forming portions 63, to be slipped through one of the drainage eyes 20. The trailing portion of the core 62 then can be withdrawn through the drainage eye, the tip assembly being sufficiently elastic and resilient to stretch over any shoulder regions and the like.

Figure 11:
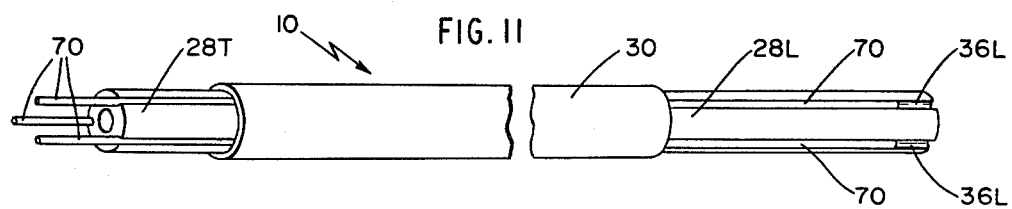
FIG. 11 illustrates the elongate catheter body before attachment to the tip with wires extending through the inflation lumens.

The elongate catheter core 28 and sleeve 30 are extruded separately, the core 28 being formed with the wholly enclosed inflation lumens 36' or the preferred plurality of longitudinally extending grooves 40 formed in its outer surface. Before the sleeve 30 and core 28 are cemented, the inflation lumens are threaded with wires 70 which will insure that the cement will not enter into and block the lumens (FIG. 11). The wires 70 may not be necessary when the inflation lumens are formed wholly within the core 28. The forward, leading ends of the wires 70 are placed to extend forwardly beyond the forward end of the outer sleeve 30 but terminate short of the forward end 28L of the inner core 28, thus leaving the forwardmost end of the lumens exposed as indicated at 36L. When assembled and cemented to the tip, these exposed portions 36L of the inflation lumens will be filled with cement as shown at 34 in FIGS. 1 and 13 to provide additional surface for secure adhesion. The rearward, trailing ends of the wires extend rearwardly and protrude beyond the trailing end 28T of the inner core 28.

Figure 12:
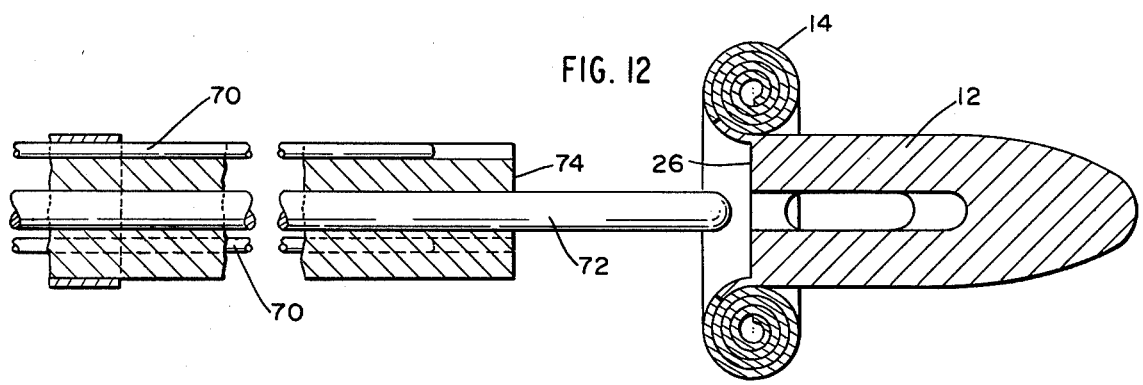
FIG. 12 is an illustration of the manner in which the leading end of the catheter body and the catheter tip are assembled.
Figure 13:
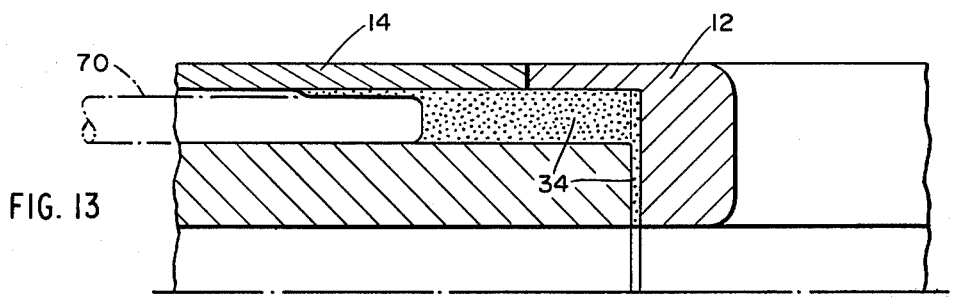
FIG. 13 is an enlarged illustration of the juncture of the leading end of the catheter body with the catheter tip.

When subsequently assembling the catheter tube 10 and tip with integral balloon, the catheter body 10 is placed on an assembly mandrel 72 which protrudes forwardly beyond the leading end 28L of the core 28 (FIG. 12). The balloon portion 14 of the tip 12 is everted as suggested in FIG. 12 and the tip is placed over the end of the mandrel 72 so that its rearwardly facing shoulder 26 abuts against the forward end 74 of the catheter core 28. The butted regions are cemented to each other by an appropriate adhsive 34 which also is applied about the leading portion of the core which will underlie the forward end of the balloon portion 14 as described above. The balloon portion 14 then is partly unrolled and cemented at its forward region to the core 28. After the juncture region of the core 28, tip 12 and balloon portion 14 have been cemented satisfactorily, the balloon portion 14 then is fully unrolled rearwardly to bring its rearward end into abutment with the forwardmost end of the catheter sleeve 30. Cement is applied to the juncture of the core 28, sleeve 30 and rear end of the balloon portion 14 and the cement is permitted to cure. It should be noted that the inflation lumen wires 70 remain in place during these cementing operations to insure that the lumens will not be obstructed by the cement.

After all the adhesive has cured the assembly mandrel 72 is removed. The funnel 16 then may be attached to the rearwardmost end of the catheter tube 10 by adhesive in a similar manner to that described above. When the catheter is of the type in which the inflation lumens are defined by the external grooves 40 on the catheter core, the rearwardmost end of the core which is received within the bore 48 of the funnel 16 should be filled with cement so that the inflating gas cannot pass from the inflation manifold 56 into the drainage lumen 24. In this embodiment, the inflation lumen wires 70 may remain in place and may be extended through the inflation branch 38 of the funnel 16. The wires 70 are subsequently removed through the inflation branch of the funnel. The adhesive which bonds the rearward end of the outer sleeve 30 to the inner surface of the bore 48 should be carefully placed. The adhesive should not enter into any of the inflation lumen grooves 40. Where the inflation lumens are formed wholly within the wall of the inner core 28 openings must be formed to communicate the inflation manifold 56 with the lumens before the trailing end of the catheter is assembled with the funnel 16. Here, again, the adhesive must be applied in a manner which will not interfere with flow through the inflation lumens.

After the tip and catheter body have been fully assembled, it may be desirable to dip the tip in liquid silicone rubber to deposit a thin "finish" coat over the tip. This may enhance the aesthetic appearnace of the tip in the event that there were any minor crevices between the balloon and shoulder of the catheter.

Thus, I have described a urethral catheter construction and technique for its manufacture which achieves significant advantages both in its use and manufacture than has been heretofore possible with prior catheters. It should be understood, however, that the foregoing description of the invention is intended merely to be illustrative thereof and that other modifications and embodiments may be apparent to those skilled in the art without departing from its spirit.

Having thus described the invention, what I desire to claim and secure by Letters Patent is:

1. A Foley-type urethral drainage catheter having a tip portion, an elongate body portion having a drainage lumen and at least one inflation lumen, the body portion extending rearwardly from the tip portion, and an inflatable balloon in communication with the inflation lumen, said catheter further comprising:

the balloon portion and tip portion being molded in a single, integral piece in which the balloon portion is formed from a material which is more elastic than that from which the tip portion is formed;

the elongate catheter body being formed from an inner core and an outer sleeve, the forward end of the inner core protruding outwardly beyond the forward end of the outer sleeve, thereby to define a peripheral shoulder at the region of attachment of the catheter body to the trailing end of the balloon portion, the shoulder being dimensioned so that the outer surface of the balloon portion merges smoothly with the outer surface of the catheter body in a shoulderless configuration.

2. A catheter as defined in claim 1 further comprising:
the inner core having the elongate drainage lumen extending therethrough;
said at least one inflation lumen being defined by elongate passageway formed between the inner core and outer sleeve of the elongate catheter body, the passageway communicating at its forward end with the interior of the balloon portion.

3. A catheter as defined in claim 2 wherein the inflation lumen passageway is defined by a longitudinally extending groove formed along the external surface of the inner core and cooperating with the inner surface of the outer sleeve.

4. In a Foley-type urethral drainage catheter having a tip portion, elongate body portion having a drainage and at least one inflation lumen, the body portion extending rearwardly from the tip portion and an inflatable balloon in communication with the inflation lumen, the improvement comprising:

the balloon portion and tip portion being molded in a single, integral piece in which the balloon portion is formed from a material which is more elastic than that from which the tip portion is formed;

the trailing end of the balloon portion being attached to the catheter body, the catheter body being formed to define a peripheral shoulder at its region of attachment to the trailing end of the balloon portion, the shoulder being dimensioned so that the outer surface of the balloon portion merges smoothly with the outer surface of the catheter body in a shoulderless configuration;

the elongate catheter body being formed from an inner core and an outer sleeve, the forward end of the inner core protruding outwardly beyond the forward end of the outer sleeve, the shoulder being defined at the forward end of the outer sleeve;

the inner core having the elongate drainage lumen extending therethrough;

said at least one inflation lumen being defined by elongate passageway formed between the inner core and outer sleeve of the elongate catheter body, the passageway communicating at its forward end with the interior of the balloon portion;

the inflation lumen passageway being defined by a longitudinally extending groove formed along the external surface of the inner core and cooperating with the inner surface of the outer sleeve;

there being a plurality of said inflation lumens extending through the elongated catheter body, the outer sleeve being sufficiently elastic and resilient so that in the event of blockage of one of the lumens, inflating gas may pass between the sleeve and inner core to another of the inflation lumens.

5. A catheter as defined in claim 4 wherein the elasticity of the sleeve is less than that of the balloon portion.

6. A method of fabricating a Foley-type urethral catheter comprising:

molding a catheter tip assembly including a tip portion and a balloon portion in a single, integral, unitary and fused piece from different parisons of fuseable and compatible silicone rubber in which the balloon portion is formed from a more elastic silicone rubber than is said tip portion, said tip portion and balloon portion being molded to form a smooth, shoulderless external surface;

attaching the one-piece tip assembly to an elongate catheter body by cementing a rearwardly disposed portion of the tip portion to the forward end of the catheter body and cementing the rearward end of the balloon portion to the forward region of the catheter body to define a smooth, shoulderless external surface.

7. A method for fabricating a tip assembly for use in the manufacture of a Foley-type urethral catheter comprising:

providing a mold having a mold cavity of generally cylindrical configuration and having a smoothly rounded forward end;

providing a mold core receivable within the mold cavity, the mold core being of generally T-shaped configuration having a main portion and a pair of transversely extending cross portions near the forward end of the mold core, the mold core and the mold cavity being of a configuration which will define a one-piece catheter tip and balloon portion extending from the catheter tip;

filling the tip region of the mold cavity with a parison of silicone rubber material which, when molded and cured will display a selected elasticity;

filling the remaining, balloon portion-defining region of the mold cavity with a silicone rubber material which, when molded and cured, will display a higher degree of elasticity than the material from which the tip portion is molded;

enclosing said core and parisons within the mold and treating the mold to cure and mold the parisons into a single, fused, integral piece of silicone rubber.

8. A method for fabricating a tip assembly for use in the manufacture of a Foley-type urethral catheter comprising:

providing a mold having a mold cavity of generally cylindrical configuration and having a smoothly rounded forward end;

providing a mold core receivable within the mold cavity, the mold core having an elongate main portion and at least one transversely extending portion near the forward end of the mold core, the mold core and the mold cavity being of a configuration which will define a one-piece catheter tip and balloon portion extending from the catheter tip;

filling the tip region of the mold cavity with a parison of silicone rubber material, which, when molded and cured, will display a selected elasticity;

filling the remaining, balloon portion-defining region of the mold cavity with another parison of silicone rubber material which, when molded and cured, will display a higher degree of elasticity than the material from which the tip portion is molded;

enclosing said core and parisons within the mold and treating the mold to cure and mold the parisons into a single, fused, integral piece of silicone rubber.

* * * * *